United States Patent
Morrow et al.

(10) Patent No.: US 7,356,849 B2
(45) Date of Patent: Apr. 15, 2008

(54) NO-SLIP ELBOW PAD

(75) Inventors: David Morrow, Farmington Hills, MI (US); Jesse Hubbard, New York, NY (US)

(73) Assignee: Warrior Lacrosse, Inc., Warren, MI (US)

( * ) Notice: Subject to any disclaimer, the term of this patent is extended or adjusted under 35 U.S.C. 154(b) by 262 days.

(21) Appl. No.: 10/187,680

(22) Filed: Jul. 2, 2002

(65) Prior Publication Data
US 2004/0003454 A1    Jan. 8, 2004

(51) Int. Cl.
    *A41D 13/08*    (2006.01)
(52) U.S. Cl. ............................................. 2/16
(58) Field of Classification Search .................... 2/455, 2/16, 24, 267, 22, 465; 248/118, 118.1; 482/905, 44; 602/62–63, 4–5, 26; 128/881
See application file for complete search history.

(56) References Cited

U.S. PATENT DOCUMENTS

| 3,561,436 A | * | 2/1971 | Gaylord, Jr. ................. 602/19 |
| 3,648,291 A | * | 3/1972 | Pankers ........................... 2/16 |
| 3,789,842 A | * | 2/1974 | Froimson ..................... 602/62 |
| 3,911,497 A | * | 10/1975 | Lewis et al. ..................... 2/16 |
| 4,014,327 A | * | 3/1977 | Spiro .......................... 602/62 |
| 4,027,666 A | * | 6/1977 | Marx ........................... 602/62 |
| 4,048,991 A | * | 9/1977 | Marx ........................... 602/64 |
| 4,120,052 A | * | 10/1978 | Butler ............................. 2/16 |
| 4,150,442 A | * | 4/1979 | Boone ........................ 602/63 |
| 4,198,708 A | * | 4/1980 | Fugere et al. .................... 2/16 |
| 4,484,361 A | | 11/1984 | Leighton et al. |
| 4,642,814 A | * | 2/1987 | Godfrey ....................... 2/462 |
| 4,922,929 A | * | 5/1990 | DeJournett .................. 128/892 |
| 5,222,256 A | | 6/1993 | Wang |
| 5,445,385 A | * | 8/1995 | Brooks ........................ 473/214 |
| 5,449,341 A | * | 9/1995 | Harris .......................... 602/63 |
| 5,451,201 A | * | 9/1995 | Prengler ...................... 602/26 |
| D364,009 S | | 11/1995 | Engdahl |
| 5,561,857 A | * | 10/1996 | Hoshizaki et al. ................ 2/22 |
| 5,594,954 A | | 1/1997 | Huang |
| 5,716,120 A | | 2/1998 | Hung |
| D396,330 S | | 7/1998 | Oetting |
| 5,781,935 A | * | 7/1998 | Bassett et al. ................. 2/455 |
| 5,865,775 A | * | 2/1999 | Peoples et al. ............... 602/20 |
| 5,887,277 A | * | 3/1999 | Lohman .......................... 2/16 |
| D407,859 S | | 4/1999 | Rule |
| 5,925,010 A | * | 7/1999 | Caprio, Jr. ................... 602/62 |

(Continued)

OTHER PUBLICATIONS

STX Lacrosse Catalog 2000; Elbow Pad.

*Primary Examiner*—Alissa Hoey
(74) *Attorney, Agent, or Firm*—Dickinson Wright PLLC

(57) ABSTRACT

A no-slip elbow pad (10) for securely fastening to a user's arm and adequately protecting the user's arm. The no-slip elbow pad (10) includes a padding element (12) having an inner lining (14) and an outer lining (16). The padding element (12) has at least two bands (18, 20) integrally connected thereto. These bands (18, 20) overlay the inner lining (14) of the padding element (12) and are intended to secure the no-slip elbow pad (10) to the user's arm. The inner lining (14) has at least one friction element (28, 30) integrated thereon. Each friction element (28, 30) is intended to engage the user's arm to prevent the no-slip elbow pad (10) from sliding out of a desired position.

29 Claims, 2 Drawing Sheets

U.S. PATENT DOCUMENTS

| | | |
|---|---|---|
| D417,036 S | 11/1999 | Hamowy |
| 6,059,834 A * | 5/2000 | Springs .................... 623/32 |
| D426,678 S | 6/2000 | Rule |
| D430,362 S | 8/2000 | Pagotto |
| 6,098,208 A * | 8/2000 | Cordon ..................... 2/455 |
| 6,122,768 A * | 9/2000 | McCrane .................... 2/16 |
| 6,128,777 A * | 10/2000 | Foreman .................... 2/16 |
| 6,138,281 A * | 10/2000 | Chiaruttini ................. 2/239 |
| 6,192,519 B1 * | 2/2001 | Coalter ..................... 2/16 |
| 6,205,583 B1 | 3/2001 | Beland |
| 6,216,268 B1 * | 4/2001 | Schleicher ................. 2/16 |
| 6,219,843 B1 * | 4/2001 | Passi et al. ................ 2/16 |
| 6,243,867 B1 * | 6/2001 | Faison ...................... 2/16 |
| 6,328,706 B1 * | 12/2001 | Yattavong .................. 602/21 |
| 6,374,408 B1 * | 4/2002 | Tomlinson et al. ............. 2/22 |
| 6,398,749 B1 * | 6/2002 | Slautterback ................ 602/62 |
| 6,503,216 B1 * | 1/2003 | Thibodo, Jr. ................ 602/21 |
| 6,654,960 B2 * | 12/2003 | Cho ........................ 2/22 |
| 6,807,680 B2 * | 10/2004 | Sloot ....................... 2/16 |
| 6,880,172 B2 * | 4/2005 | Quintero .................... 2/16 |
| 2002/0138896 A1 * | 10/2002 | Holden ..................... 2/267 |
| 2003/0028947 A1 * | 2/2003 | Fee et al. ................... 2/16 |
| 2004/0045079 A1 * | 3/2004 | Quintero .................... 2/455 |

* cited by examiner

NO-SLIP ELBOW PAD

TECHNICAL FIELD

The present invention relates generally to an elbow pad for protecting the elbow joint and the areas directly above and below the elbow joint, and more particularly to a no-slip elbow pad adapted for remaining effectively locked in a position for protecting the elbow joint and the adjacent areas.

BACKGROUND OF THE INVENTION

It is widely known that the participants of various sports use elbow pads and other protective gear for preventing potential injuries characteristic of the sport. For instance, a typical lacrosse player wears an elbow pad for cushioning blows normally imparted upon his arms, such as when he is slashed in the arm by an opponent, when he falls to the ground and lands on his elbow, or when he bumps into another player. Hockey players also wear elbow pads for protective purposes, including to cushion the impact of a fall to the ice, of hitting the boards or the goalposts, as well as to protect from injury if hit by a stick or a puck.

A typical elbow pad includes a one piece padding element composed of a spongy energy absorbing material. The padding element covers the elbow joint and the adjacent areas above and below the elbow joint.

Usually, the padding element has a pair of elastic bands that are sewn or otherwise connected to the padding element. These elastic bands are typically intended to stretch against the user's upper arm and forearm for the purpose of securing the elbow pad to the participant's arm.

These elastic bands substantially stretch against the user's arm only while the arm is in a bent position. However, when the user's arm is straightened, the elastic bends may not be sufficiently stretched against the arm so as to secure the elbow pad in a fixed position. Consequently, the elbow pad may slide down the user's arm thereby exposing the upper arm and elbow joint to potential injury or simply causing discomfort. This sort of undesired movement typically occurs when the user repeatedly and/or forcefully bends and straightens his arms, e.g. while running or throwing a lacrosse ball or shooting or passing a hockey puck. Consequently, a user must constantly readjust the elbow pad to place it in a position for protecting the elbow joint in a manner that is comfortable to the user.

In addition, some elbow pads may include one or more adjustable straps that may further tighten the fit of the elbow pad on the user's arm. If the adjustable straps are sufficiently tightened, the elbow pad may not slide down the user's arm. However, this level of tension makes it difficult for the user to repeatedly bend his arm without an appreciable level of discomfort or exhaustion of his arm muscles.

Therefore, there is a need for a no-slip elbow pad that provides adequate protection against arm injuries while the user makes sudden, forceful arm movements without the need for constant adjustment.

SUMMARY OF THE INVENTION

It is therefore an object of the present invention to provide an elbow pad, which remains effectively locked in a desired position on a user's arm despite sudden forceful and/or repetitious arm movements that may otherwise cause the elbow pad to propagate down the user's arm.

It is another object of the present invention to provide an elbow pad, which stays in place and permits a user to focus his attention on an ongoing game or any other ongoing activity.

It is yet another object of the present invention to provide an elbow pad, which has a relatively light weight for improving a user's performance in a sporting event or any other ongoing activity that requires arm protection.

It is still another object of the present invention to provide an elbow pad, which has a simple design that reduces manufacturing time and costs associated therewith.

In accordance with the above and other objects of the present invention, a no-slip elbow pad is provided for securely fastening to a user's arm and adequately protecting the user's arm. The no-slip elbow pad includes a padding element having an inner lining and an outer lining. The padding element has at least two bands integrally connected thereto. These bands overlay the inner surface of the padding element and are intended to secure the no-slip elbow pad to the user's arm. The inner side has at least one friction element integrated thereon. Each friction element is intended to engage the user's arm to prevent the elbow pad from sliding out of a desired position.

One advantage of the present invention is that the no-slip elbow pad is effectively locked in a position on a user's arm, despite sudden forceful arm movements.

Another advantage of the present invention is that a user will not be distracted by undesired movement of an elbow pad or any resulting need to readjust the elbow pad.

Yet another advantage of the present invention is that the no-slip elbow pad is relatively light weight thereby decreasing the amount of energy a user expends on wearing the elbow pad and allowing the user to exert more energy on other activities.

Other advantages of the present invention will become apparent when viewed in light of the detailed description of the preferred embodiment when taken in conjunction with the attached drawings and appended claims.

BRIEF DESCRIPTION OF THE DRAWINGS

For a more complete understanding of this invention, reference should now be made to the embodiments illustrated in greater detail in the accompanying drawings and described below by way of examples of the invention.

DETAILED DESCRIPTION OF THE PREFERRED EMBODIMENT

Figures 1, 2, 4A:
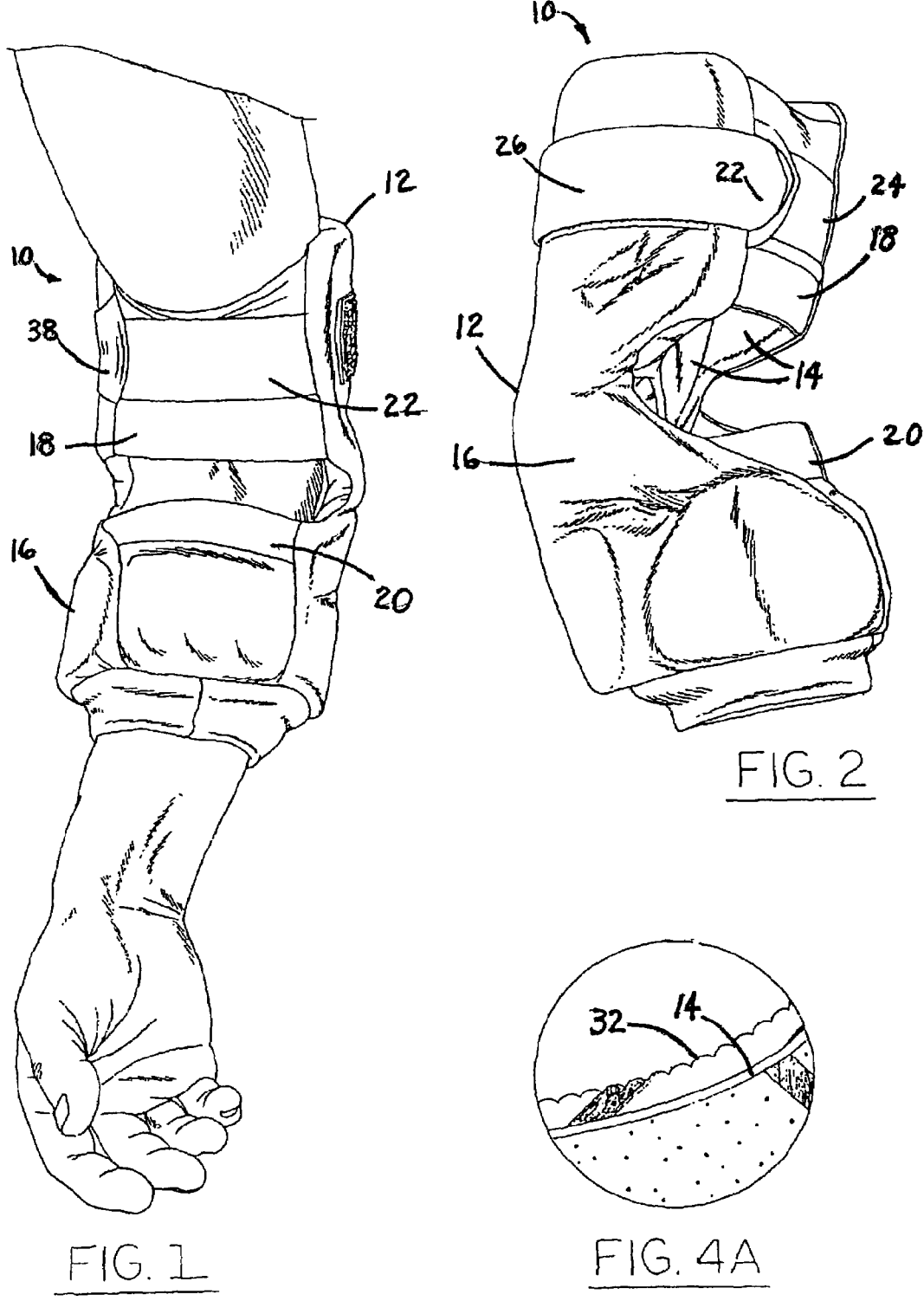
FIG. 1 is a perspective view of a no-slip elbow pad worn on the arm of a user, in accordance with a preferred embodiment of the present invention.
FIG. 2 is a side view of a no-slip elbow pad, in accordance with a preferred embodiment of the present invention.
FIG. 4A is a magnified cross-sectional view of the friction element having a no-slip textured surface as shown in FIG. 4, taken within circle 4A.

In the following figures, the same reference numerals are used to identify the same components in the various views.

Referring primarily to FIGS. 1 and 2, a no-slip elbow pad 10 is provided for protecting a user's elbow joint and the areas directly above and below the elbow joint. The no-slip elbow pad 10 includes a padding or protective element 12 having an inner lining 14 and an outer lining 16. The padding element 12 includes a plurality of arm protectors contained between the inner lining 14 and the outer lining 16. The padding element 12 extends along a longitudinal axis 50 between upper and lower ends 52, 54 with at least two edges 56, 58 disposed on opposite sides of the longitudinal axis 50.

As is known in the art, these arm protectors absorb or deflect the kinetic energy of blows delivered to the user's arm. To accomplish this, the arm protectors may be made of spongy energy absorbing materials such as foam, rigid shells, a combination thereof, or other suitable materials that protect the user's arm.

In this regard, the no-slip elbow pad 10 is beneficial to an individual performing any activity that may result in injury to his or her arm. By way of illustration, a lacrosse player may use the no-slip elbow pad 10 to protect his arm from injuries that would otherwise result when he is slashed in the arm by an opponent or when he falls to the ground and lands on his arm. The no-slip elbow pad 10 is preferably for use as an athletic protective device in sports, such as lacrosse and hockey, but may be utilized for a variety of other purposes. Moreover, while the no-slip features of the present invention are preferably applicable to elbow pads, they may also be utilized with any other type of protective equipment.

As shown, the no-slip elbow pad 10 preferably includes an upper elastic band 18 and a lower elastic band 20 for securing the no-slip elbow pad 10 to a user's arm. The upper and lower elastic bands 18, 20 are discrete from, and integrally connected with, respectively, upper and lower portions of the padding element 12 along two edges 56, 58 of the element 12 so as to overlay the inner lining 14. The user may wear the no-slip elbow pad 10 by sliding his arm between the inner lining and the elastic bands 18, 20.

In addition to the upper and lower elastic bands 18, 20, the no-slip elbow pad 10 also preferably includes an adjustable strap 22 that tightens or loosens the fit of the elbow pad 10 on the user's arm. The strap 22 has a posterior side facing toward the inner lining 14. Preferably, the adjustable strap 22 has a first end 24 sewn or otherwise connected to the upper portion of the padding element 12. The adjustable strap 22 is preferably held adjacent to the upper portion of the padding element 12 by a ring 38 sewn or otherwise connected to the upper portion of the padding element 12.

Furthermore, the adjustable strap 22 preferably has a second end 26 with a hook fastener pad (not shown) integrated thereon. The hook fastener pad is intended to fasten to a loop pad 40 attached to the outer lining 16 of the padding element 12. However, various other kinds of opposing fasteners may be used to tighten the adjustable strap 22 at different tension levels.

The user may tighten the adjustable strap 22 to a suitable tension level for assisting the upper and lower elastic bands 18, 20 in securing and retaining the no-slip elbow pad 10 to the user's arm without causing discomfort to the user's arm or making him waste unnecessary energy in bending his arm.

Figure 4:
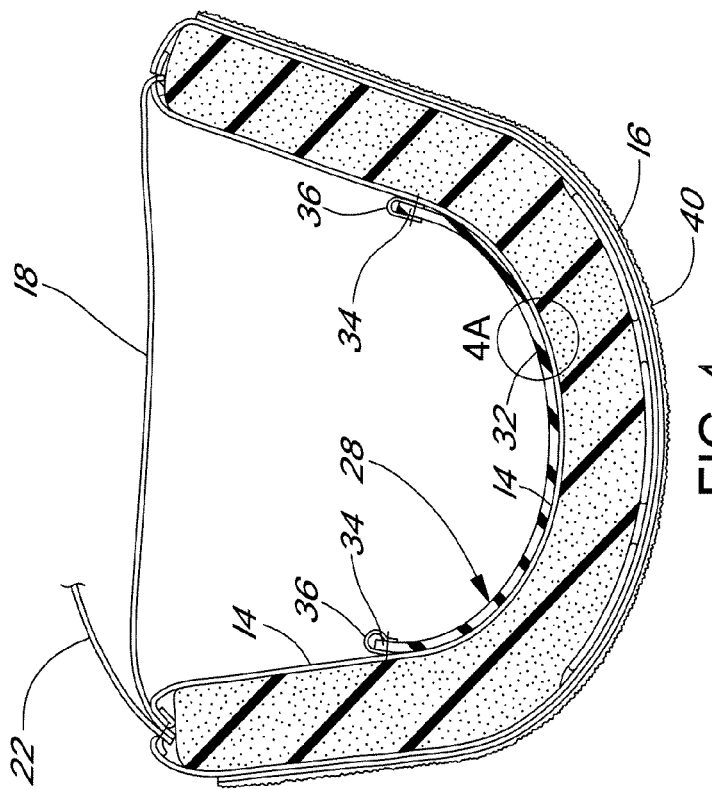
FIG. 4 is a cross-sectional view of the no-slip elbow pad as shown in FIG. 3, taken along line 4-4.
Figure 3:
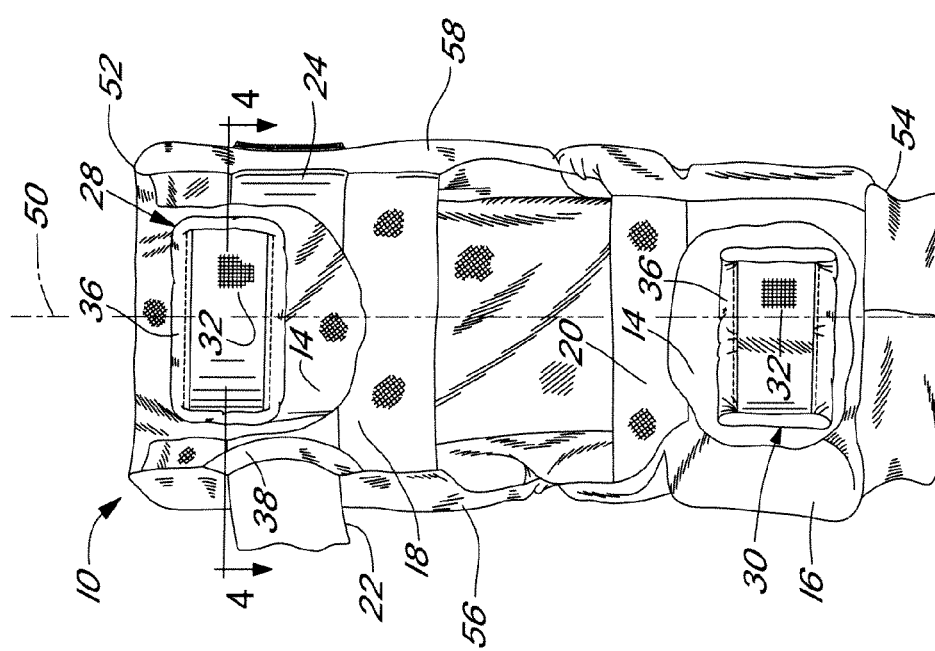
FIG. 3 is a partially cut-away front view of a no-slip elbow pad, in accordance with a preferred embodiment of the present invention.

Referring now primarily to FIGS. 3, 4, and 4A, the no-slip elbow pad 10 preferably includes an upper friction component or element 28 and a lower friction component or element 30. The friction elements 28, 30 define a greater coefficient of friction that the inner lining 14 to enhance holding of the no-slip elbow pad 10 in a desired position with respect to a wearer's arm The exemplary elements 28, 30 are of generally rectangular shape and non-removable from the inner lining 14. Preferably, the upper and lower friction elements 28, 30 are discrete from, and integrated or connected with, respectively, on the upper and lower portions of the inner lining 14. The friction elements 28, 30 are discrete from the bands 18, 20. These upper and lower portions are in substantial contact with the user's arm when the arm is straightened. Therefore, each friction element 28, 30 is properly positioned for contacting the user's arm and preventing the no-slip elbow pad 10 from sliding out of the desired position. The friction element 28 is spaced from the band 18 along the longitudinal axis 50. The friction element 30 is spaced closer to the lower end 54 than the band 20. While two friction elements 28, 30 are disclosed, it will be understood that any number of friction pads may be utilized, including more or less than than two. FIG. 4A shows that the inwardly-facing surface 32 of the friction element 30 and the inwardly-facing surface of the inner lining 14 have different textures. The surface 32 is raised and bumpy, with a repeating pattern of ridges and valleys.

Unlike the elastic bands 18, 20, these friction elements 28, 30 can easily hold the no-slip elbow pad 10 in a desired position while the user's arm is straightened. Moreover, unlike the adjustable strap 22, the upper and lower friction elements 28, 30 can effectively lock the no-slip elbow pad 10 in a desired position without causing discomfort to the user or demanding increased effort in bending the elbow pad.

Preferably, each friction element 28, 30 is comprised of a pad of neoprene rubber with a textured surface 32 for creating ample friction between the friction element 28, 30 and the user's arm. However, it is understood that each friction element 28, 30 may be made of other suitable no-slip materials that have a variety of different surface textures, including smooth surface textures. It will be understood that the friction elements 28, 30 can be constructed of any suitable material and can take on a variety of different configurations. The friction elements however are intended to create friction between the protective padding and a wearer's skin to minimize movement therebetween and thereby provide increased protection.

As best shown in FIGS. 3 and 4, each friction element 28, 30 includes a border 34 for attaching each of the friction elements 28, 30 to the inner lining 14 of the padding element 12. The border 34 is sewn or otherwise connected to the inner lining 14. However, the friction elements 28, 30 can be attached to the inner lining 14 by a variety of different attachment methods.

Furthermore, the border 34 of each friction element 28, 30 is preferably covered with a border guard 36 for reducing wear on the friction elements 28, 30. Specifically, the border guard 36 prevents each friction element 28, 30 from tearing at its border 34.

While particular embodiments of the invention have been shown and described, numerous variations and alternate embodiments will occur to those skilled in the art. Accordingly, it is intended that the invention be limited only in terms of the appended claims.

What is claimed is:

1. A no-slip elbow pad comprising:
    a padding element having an inner lining operable to engage an arm of a user, at least two edges and an outer lining;
    at least one band connected to said at least two edges and overlaying said inner lining of said padding element and operable to allow the arm of the user to be received between said at least one band and said inner lining of said padding element;

at least one friction element coupled to said inner lining of said padding element, wherein said at least one friction element and said inner lining define different coefficients of friction such that said at least one friction element defines a greater coefficient of friction than said inner lining and is thereby more operable to minimize movement of said elbow pad on the arm of the user than said inner lining; and a border guard at least partially encircling a border of said friction element for attachment to said inner lining, said border guard for protecting said at least one friction element against tearing from said inner lining.

2. The no-slip elbow pad of claim 1 wherein said padding element is further defined as extending along a longitudinal axis between upper and lower ends with said at least two edges disposed on opposite sides of said longitudinal axis and wherein said at least one friction element is integrated within an area of said inner lining of said padding element adjacent to said upper end and is spaced from said at least one band along said longitudinal axis.

3. The no-slip elbow pad of claim 1 wherein said padding element is further defined as extending along a longitudinal axis between upper and lower ends with said at least two edges disposed on opposite sides of said longitudinal axis and wherein said at least one friction element is integrated within an area of said inner lining of said padding element adjacent to said lower end and is spaced closer to said lower end than said at least one band.

4. The no-slip elbow pad of claim 1 wherein said at least one friction element has an inwardly-facing surface operable to contact the arm of the user and defining a first texture and said inner lining has an inwardly-facing surface operable to contact the arm of the user and defining a second texture different than said first texture.

5. The no-slip elbow pad of claim 1 wherein said at least one friction element is comprised of a neoprene rubber.

6. The no-slip elbow pad of claim 1 wherein said at least one band further comprises at least two bands including a lower elastic band connected to said at least two edges of a lower portion of said padding element and an upper elastic band connected to said at least two edges of an upper portion of said padding element, wherein said at least one friction element is spaced from both of said lower and upper bands along a longitudinal axis of said padding element.

7. A no-slip protective pad comprising:
a padding element extending along a longitudinal axis and having an upper portion coupled to a lower portion and including an inner lining operable to contact an arm of a user and an outer lining, said padding element having a padded portion disposed between said inner lining and said outer lining;
an adjustable strap having a posterior side connected to said padding element and facing said inner lining of said padding element, said adjustable strap for retaining the no-slip pad to a user's arm;
an upper friction element disposed on said inner lining of said upper portion of said padding element, said upper friction element being constructed of a rubber material and being non-removably attached to said inner lining of said padding element;
a lower friction element disposed on said inner lining of said lower portion of said padding element, said lower friction element being constructed of a rubber material and being non-removably attached to said inner lining of said padding element;

wherein one of said upper friction element and said lower friction element is spaced from said adjustable strap along said axis as well as non-removable from said padding element.

8. The no-slip pad of claim 7 wherein said upper friction element and said lower friction element each have a textured surface for contacting said user and minimizing movement of the no-slip pad on said user.

9. The no-slip pad of claim 7 wherein said upper friction element and said lower friction element are comprised of a neoprene rubber.

10. The no-slip pad of claim 9 wherein said upper friction element and said lower friction element each include a border for attachment to said inner lining.

11. The no-slip pad of claim 10 wherein said border is covered with a border guard for protecting said neoprene rubber from tearing.

12. The no-slip pad of claim 7 further comprises:
a lower elastic band integrally connected to said lower portion of said padding element; and
an upper elastic band integrally connected to said upper portion of said padding element, wherein said lower friction element is spaced from said lower elastic band along said axis and said upper friction element is spaced from said upper elastic band along said axis.

13. A no-slip protective pad comprising:
a padding element having an inner lining operable to contact an arm of a user and an outer lining, at least a portion of said inner lining having a friction component coupled to said inner lining, said friction component being discrete from said inner lining and operable to contact a portion of the user's arm to minimize movement of said no-slip pad on the user's arm, said friction component and said inner lining defining different coefficients of friction such that said friction component has a greater coefficient and is thus more operable to minimize movement of said no-slip protective pad on the arm of the user than said inner lining;
a border guard covering a border of said friction component for protecting said friction component from tearing; and
an elastic band connected to said padding element and facing said inner lining of said padding element and spaced from said friction element, said elastic band being discrete from said friction component wherein the user's arm is receivable between said elastic band and said friction component and said inner lining.

14. The no-slip pad of claim 13 wherein said friction component is comprised of a neoprene rubber.

15. The no-slip pad of claim 13 wherein said friction component has a textured surface for contacting the portion of the user and minimizing movement of said no-slip pad on the user.

16. The no-slip pad of claim 13 further comprising:
an adjustable strap integrally connected to an upper portion of said padding element.

17. The no-slip pad of claim 16 further comprising a ring for holding said adjustable strap in a desired position.

18. A pad for engagement with a wearer's arm comprising:
a padded portion extending along a longitudinal axis generally between a wearer's forearm and bicep, said padded portion having an inner lining, an outer lining, and at least one absorbing pad disposed therebetween, said padded portion having an upper arm portion coupled to a lower arm portion;

a plurality of elastic bands overlaying said padded portion, including at least upper and lower elastic bands wherein said upper elastic band is secured to said padded portion adjacent said upper arm portion and facing said inner lining thereby allowing the wearer's arm to pass between said inner lining and an underside of said upper elastic band to retain said padded portion to said wearer's arm and wherein said lower elastic band is secured to said padded portion adjacent said lower arm portion and overlying said inner lining allowing the wearer's arm to pass between said inner lining and an underside of said lower elastic band to retain said padded portion to the wearer's arm; and at least one friction element formed of neoprene secured to said inner lining to minimize movement of said padded portion with respect to said wearer's arm and spaced from all of said plurality of elastic bands along said axis and not overlayed.

19. The pad of claim 18 further comprising:
an adjustable strap to assist in adjusting the fit of said padded element to the wearer's arm.

20. The pad of claim 18 wherein said at least one friction element includes a raised and bumpy textured surface to further enhance the no-slip characteristics of said pad.

21. The pad of claim 18 wherein said at least one friction element is sewn to said inner lining.

22. The pad of claim 18 wherein a plurality of friction elements are secured to said inner lining.

23. The pad of claim 18 wherein said at least one friction element is secured to said inner lining adjacent said upper elastic band adjacent to an upper end of the padded portion.

24. The pad of claim 18 wherein said at least one friction element is secured to said inner lining adjacent said lower elastic band between said lower elastic band and a lower end of the padded portion along said longitudinal axis.

25. A pad for engagement with a wearer's arm comprising:
a protective element extending generally between a wearer's forearm and bicep and covering a wearer's elbow, said protective element having an inner lining, an outer lining, and at least one absorbing pad disposed therebetween;

at least one elastic band connected to said protective element and overlaying said inner lining, said at least one elastic band allowing a wearer's arm to slide between said inner lining and an underside of said at least one elastic band to retain said protective element to said wearer's arm;

at least one friction element formed from neoprene and non-removably secured to said inner lining to minimize movement of the pad with respect to said wearer's arm, said at least one friction element being discrete from said at least one elastic band and defining a greater coefficient of friction than said inner lining.

26. The pad of claim 25 wherein said at least one friction element is generally rectangular in shape.

27. The pad of claim 25, wherein said friction element has a generally raised textured surface with a repeating pattern of ridges and valleys.

28. The pad of claim 25, wherein a plurality of friction elements are secured to said inner lining.

29. The pad of claim 25, further comprising:
an adjustable strap to assist in adjusting the fit of said protective element to the wearer's arm, said adjustable strap secured to said protective element.

* * * * *